(12) United States Patent
Osman et al.

(10) Patent No.: US 9,849,245 B2
(45) Date of Patent: Dec. 26, 2017

(54) PEN-TYPE INJECTOR

(71) Applicant: SANOFI-AVENTIS DEUTSCHLAND GMBH, Frankfurt am Main (DE)

(72) Inventors: Thomas Frederick Osman, Warwickshire (GB); David Sanders, Warwickshire (GB)

(73) Assignee: SANOFI-AVENTIS DEUTSCHLAND GMBH, Frankfurt am Main (DE)

( * ) Notice: Subject to any disclaimer, the term of this patent is extended or adjusted under 35 U.S.C. 154(b) by 49 days.

(21) Appl. No.: 14/388,549

(22) PCT Filed: Apr. 2, 2013

(86) PCT No.: PCT/EP2013/056852
§ 371 (c)(1),
(2) Date: Sep. 26, 2014

(87) PCT Pub. No.: WO2013/149979
PCT Pub. Date: Oct. 10, 2013

(65) Prior Publication Data
US 2015/0057619 A1 Feb. 26, 2015

Related U.S. Application Data

(60) Provisional application No. 61/666,269, filed on Jun. 29, 2012.

(30) Foreign Application Priority Data

Apr. 5, 2012 (EP) .................... 12163484

(51) Int. Cl.
*A61M 5/24* (2006.01)
*A61M 5/32* (2006.01)
*A61M 5/31* (2006.01)

(52) U.S. Cl.
CPC ............ *A61M 5/24* (2013.01); *A61M 5/3134* (2013.01); *A61M 5/3202* (2013.01);
(Continued)

(58) Field of Classification Search
CPC .. A61M 2005/2488; A61M 2005/2403; A61M 2005/2411; A61M 2005/2407;
(Continued)

(56) References Cited

U.S. PATENT DOCUMENTS 533,575 A 2/1895 Wilkens
2,826,195 A * 3/1958 Ashkenaz ............... A61M 5/24
604/193

(Continued)

FOREIGN PATENT DOCUMENTS

EP 0937471 8/1999
EP 0937476 8/1999

(Continued)

OTHER PUBLICATIONS

International Search Report for Int. App. No. PCT/EP2013/056852, completed May 28, 2013.

(Continued)

*Primary Examiner* — Andrew Gilbert
*Assistant Examiner* — Nilay Shah
(74) *Attorney, Agent, or Firm* — McDonnell Boehnen Hulbert & Berghoff LLP

(57) ABSTRACT

The present invention is directed to a pen-type injector equipped with a cartridge holder for a drug delivery device. The cartridge holder has a longitudinal axis and comprises a body for receiving a cartridge, wherein the body comprises at a proximal end engagement means for releasably coupling the cartridge holder to the drug delivery device, a latch member for releasably engaging a cap of the drug delivery device and an alignment element which is visual from the (Continued)

outer side of the body. The alignment element may be an aperture provided in the body and/or a lug which forms the latch member.

16 Claims, 1 Drawing Sheet

(52) U.S. Cl.
CPC ............... *A61M 2005/2403* (2013.01); *A61M 2005/2488* (2013.01); *A61M 2005/3126* (2013.01); *A61M 2205/59* (2013.01)

(58) Field of Classification Search
CPC ............ A61M 2005/2485; A61M 5/24; A61M 2005/3104; A61M 5/20; A61M 5/31591
See application file for complete search history.

(56) References Cited

U.S. PATENT DOCUMENTS

| | | | |
|---|---|---|---|
| 5,226,895 A | | 7/1993 | Harris |
| 5,244,465 A | * | 9/1993 | Michel .................... A61M 5/24 |
| | | | 604/187 |
| 5,279,586 A | | 1/1994 | Balkwill |
| 5,304,152 A | | 4/1994 | Sams |
| 5,320,609 A | | 6/1994 | Haber et al. |
| 5,383,865 A | | 1/1995 | Michel |
| 5,480,387 A | | 1/1996 | Gabriel et al. |
| 5,505,704 A | | 4/1996 | Pawelka et al. |
| 5,569,189 A | * | 10/1996 | Parsons ............... A61M 5/1782 |
| | | | 604/22 |
| 5,582,598 A | | 12/1996 | Chanoch |
| 5,626,566 A | | 5/1997 | Petersen et al. |
| 5,674,204 A | | 10/1997 | Chanoch |
| 5,688,251 A | | 11/1997 | Chanoch |
| 5,873,861 A | * | 2/1999 | Hitchins ........... A61M 5/14546 |
| | | | 604/152 |
| 5,921,966 A | | 7/1999 | Bendek et al. |
| 5,961,495 A | | 10/1999 | Walters et al. |
| 6,004,297 A | | 12/1999 | Steenfeldt-Jensen et al. |
| 6,193,698 B1 | | 2/2001 | Kirchhofer et al. |
| 6,210,369 B1 | * | 4/2001 | Wilmot ............... A61M 5/2033 |
| | | | 604/157 |
| 6,221,046 B1 | | 4/2001 | Burroughs et al. |
| 6,235,004 B1 | | 5/2001 | Steenfeldt-Jensen et al. |
| 6,248,095 B1 | | 6/2001 | Giambattista et al. |
| 6,899,698 B2 | | 5/2005 | Sams |
| 6,936,032 B1 | | 8/2005 | Bush, Jr. et al. |
| 7,241,278 B2 | | 7/2007 | Moller |
| 2002/0052578 A1 | | 5/2002 | Moller |
| 2002/0120235 A1 | | 8/2002 | Enggaard |
| 2003/0050609 A1 | | 3/2003 | Sams |
| 2004/0059299 A1 | | 3/2004 | Moller |
| 2004/0087906 A1 | * | 5/2004 | Henderson .......... A61M 5/3134 |
| | | | 604/187 |
| 2004/0210199 A1 | | 10/2004 | Atterbury et al. |
| 2004/0267207 A1 | | 12/2004 | Veasey et al. |
| 2005/0113765 A1 | | 5/2005 | Veasey et al. |
| 2006/0153693 A1 | | 7/2006 | Fiechter et al. |
| 2009/0275916 A1 | | 11/2009 | Harms et al. |
| 2010/0137809 A1 | | 6/2010 | Tschirren et al. |
| 2012/0209213 A1 | * | 8/2012 | Theucher ................ A61M 5/24 |
| | | | 604/208 |

FOREIGN PATENT DOCUMENTS

| | | | | |
|---|---|---|---|---|
| EP | 2201974 | | 6/2010 | |
| JP | 2012-504440 A | | 2/2012 | |
| RU | 2387461 C2 | | 4/2010 | |
| WO | 99/38554 | | 8/1999 | |
| WO | 01/10484 | | 2/2001 | |
| WO | 2010/037828 | | 4/2010 | |
| WO | WO 2010037828 A1 | * | 4/2010 | ........ A61M 5/31525 |
| WO | 2010/139634 | | 12/2010 | |
| WO | 2011/068542 | | 6/2011 | |
| WO | 2011/121003 | | 10/2011 | |

OTHER PUBLICATIONS

International Preliminary Report on Patentability for Int. App. No. PCT/EP2013/056852, dated Jun. 24, 2014.
Japanese Office Action for Japanese Patent Application No. 2015-503845, dated Jan. 4, 2017.
Russian Office Action for Russian Application No. 2014144353/14(071583), completed Feb. 7, 2017.

* cited by examiner

PEN-TYPE INJECTOR

CROSS REFERENCE TO RELATED APPLICATIONS

The present application is a U.S. National Phase Application pursuant to 35 U.S.C. §371 of International Application No. PCT/EP2013/056852 filed Apr. 2, 2013, which claims priority to European Patent Application No. 12163484.4 filed Apr. 5, 2012 and U.S. Provisional Patent Application No. 61/666,269, filed Jun. 29, 2012. The entire disclosure contents of these applications are herewith incorporated by reference into the present application.

TECHNICAL FIELD

The invention refers to a pen-type injector equipped with a cartridge holder. The cartridge holder has a longitudinal axis and comprises a body for receiving a cartridge. The body comprises engagement means at a proximal end for releasably coupling the cartridge holder to the drug delivery device, at least one latch member for releasably engaging a cap of the drug delivery device and at least one alignment element which is visual from the outer side of the body.

BACKGROUND

Pen-type injectors are regularly used by persons who do not have formal medical training. Accordingly, the application comes along with circumstances that set a number of requirements for drug delivery devices of this kind. In case of improper use such as unintended disassembly actions there is the risk of malfunction and contamination of the medicament stored in the cartridge. Also mechanical parts of the device could be damaged. Therefore, the device must be robust in construction in order to prevent manipulation of the components. Especially with regard to the cartridge holder, which is connected to the housing of the drug delivery device, there is demand for a reliable connection easy to manufacture and to assemble but also safe regarding to any kind of manipulation or malfunction.

The main function of a cartridge holder is to encase and fix a cartridge or an ampoule to the mechanical components of a drug delivery device such that a medicinal product contained within the cartridge can be expelled by e.g. forwarding a piston. A cartridge holder may either be permanently attached to the drug delivery device such that the drug delivery device has to be discarded if the cartridge is empty or the drug delivery device is a reusable device which allows detaching the cartridge holder to replace an empty cartridge by a new one. In the latter case it is inevitable to ensure that the cartridge holder is fully and firmly attached to the drug delivery device after replacing an empty cartridge. In other words, to achieve correct and save function, it is important that users of such pen injectors ensure that the cartridge holder is fully engaged with the device mechanism before doses are dispensed.

As an example, reusable pen injectors are known in which the cartridge holder is attached to the drug delivery device mechanism by means of a helical thread or a bayonet. Further, it is known to provide visual features on the drug delivery device and/or on the cartridge holder to assist users in determining when the cartridge holder is fully engaged. Typically, such visual features are provided on the outer surfaces of both the cartridge holder and an outer housing of the drug delivery device that line-up with each other only if the cartridge holder is fully locked to the drug delivery device.

In addition to such visual alignment features, the outer surfaces of known cartridge holders are typically provided with a range of visual features. On one side there is usually a cartridge contents scale which is often printed or laser marked onto the cartridge holder. On other sides there may be an aperture or windows to permit viewing the cartridge components, a product name and a manufacturer's logo. In addition, detent features or a latch member for releasable engaging a cap of the drug delivery device may be provided on the cartridge holder. Thus, in some cases there might be a visual clutter on the external surface of a cartridge holder which may confuse the user.

WO 2010/037828 A1 discloses an assembly comprising a drug delivery device and a monitoring device adapted to detect an action taking place in the drug delivery device. The drug delivery device comprises a main portion with coupling means for a cover. The monitoring device comprises a housing portion, means for detecting an action taking place in the drug delivery device, and coupling means adapted to engage the coupling means on the main portion. By this arrangement the monitoring device can be placed in a pre-determined position relative to the main portion when the coupling means engage each other, thus allowing transmission of information between the monitoring device and the main portion. As the cover and the monitoring device use the same coupling means for attachment on the main portion, either the cover or the monitoring device may be attached at the same time. The coupling means, thus, has the single function of attaching on of said components.

SUMMARY

It is an object of the present invention to provide a pen-type injector with a detachable cartridge holder which are especially suitable for a reusable drug delivery device and which allow a reliable assembly even by unskilled users. The invention further aims at providing a cartridge holder which is simplified with respect to the mold construction and/or the number of printing operations required in production.

This is obtained by a pen-type injector as defined in claim 1. The main aspect of the invention is the use of either an aperture or a cap retaining latch member of the cartridge holder as an alignment member. In other words, the aperture or the cap retaining latch member has a double function, thus reducing the number of separate elements on the cartridge holder.

Preferably, the latch member is the alignment member and at the same time the cap retaining member, thus fulfilling two different functions independent from each other at the same time. For example, the alignment of the cartridge holder to the housing may be kept either with the cap attached or detached. In other words, it is not required to misalign the cartridge holder and the housing for attaching or detaching the cap. Further, if the cartridge holder is detachable from the housing, the injector or drug delivery device may be a re-usable device which allows to exchange an empty cartridge by a new one.

The present invention is based on the idea that the function of the visual alignment feature which has to be provided on the cartridge holder is combined with an aperture or window in the cartridge holder and/or a latch member or detent feature for retaining the cap of the drug delivery device. For example, the alignment element which is visual from the outer side of the body of the cartridge holder may have the form of a lug which constitutes the latch member for releasably engaging the cap of the drug delivery device.

According to a first embodiment of the invention, the cartridge holder visual alignment feature also serves as a cap detent feature. In the assembled state of the cartridge holder and the drug delivery device, the cap may be retained on the cartridge holder by corresponding catch or snap features provided on the cartridge holder and the cap, respectively. Preferably, the lug has a trapezoidal (blunted triangle) or triangular shape in a cross section parallel to the longitudinal axis of the cartridge holder. Further, the lug may have the form of an arrow or any other form, suitable to indicate a position of the lug relative to another visual alignment feature. The e.g. triangular shaped lug is preferably arranged such that a tip of the lug is facing towards the proximal end of the body and a side of the triangular lug is facing towards the distal end of the body. The triangular shape of the lug assists users in recognizing the correct alignment condition of the cartridge holder relative to the drug delivery device.

To facilitate the function of the cap being snapped into place on the cartridge holder, the lug may have a chamfered outer surface such that the height of the lug increases in the direction of the longitudinal axis of the cartridge holder from the distal end to the proximal end. In addition or as an alternative, the lug may be provided on its outer surface with a cranked region or a protrusion.

In a second embodiment of the present invention, the cartridge holder alignment feature also serves as a cartridge grip aperture. The cartridge grip aperture may be a hole that is intended to allow users to retain control over the location of the cartridge when fitting or removing the cartridge holder from the housing of the drug delivery device to reduce the risk that the cartridge is inadvertently dropped. Preferably, the aperture is a long hole or a slot having a longitudinal axis which is orientated parallel to the longitudinal axis of the cartridge holder.

The body of the cartridge holder may consist of a transparent or translucent material to allow a user to view the cartridge content. In addition or as an alternative a hole or slot may be provided in the cartridge holder to partly expose the cartridge. In this respect it is preferred if the cartridge holder is provided with a cartridge contents scale on the outer surface of the body. Preferably, the contents scale is printed or laser marked onto the cartridge holder.

A pen-type injector according to the present invention may have a housing, a cap and a cartridge holder, wherein the housing is provided with engagement means for releasably coupling the cartridge holder to the drug delivery device and with an alignment element which is arranged such that it faces the alignment element of the body if the cartridge holder is fully attached to the housing via the engagement means. The housing of the pen-type injector may be an outer shell of the drug delivery device encasing at least partly mechanical components of the device. The housing may further be an inner housing provided at least in part within the outer shell of the drug delivery device or may be an insert fixed to an inner or outer housing of the drug delivery device. The present invention is not limited to embodiments, where the alignment element and the engagement means are provided on a single component. For example, the alignment element may be provided on an outer shell (housing) of the pen-type injector, whereas the engagement means may be provided on an inner housing or insert.

Preferably, the alignment element of the pen-type injector has an identical or at least similar form and/or color as the alignment element of the cartridge holder. This assists users in recognizing the correct alignment condition. The alignment element of the pen-type injector may be a protrusion, a recess or an e.g. colored marking.

In addition to the visual alignment elements provided on the pen-type injector and the body of the cartridge holder, features may be provided to give users a tactile and/or audible feedback if the cartridge holder is fully attached to the housing.

According to a preferred embodiment, the cap is provided with an annular notch on its inner surface for receiving the latch member of the body. A cap may be provided as a sleeve-like element which is closed on its distal end and open on its proximal end. Preferably, the annular notch or groove is provided in the vicinity of the proximal end.

The engagement means for retaining the cartridge holder on the pen-type injector may comprise a helical thread or a bayonet.

It is preferred if the pen-type injector is a resettable injection device allowing to detach the cartridge holder. The drive mechanism of the pen-type injector may further include a piston rod which can be pushed back or wound back for replacing an empty cartridge by a new one.

It is preferred to provide a cartridge containing a medicinal product such as a medicament within the cartridge holder. The term "medicament", as used herein, means a pharmaceutical formulation containing at least one pharmaceutically active compound, wherein in one embodiment the pharmaceutically active compound has a molecular weight up to 1500 Da and/or is a peptide, a protein, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(02)25, Asp28] Exendin-4(1-39),
des Pro36 [Met(O)14 Trp(02)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;

or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5-des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(02)25, Asp28] Exendin-4(1-39)-Lys6-NH2,
H-des Asp28 Pro36, Pro37, Pro38 [Trp(02)25] Exendin-4(1-39)-NH2,
H-(Lys)6-des Pro36, Pro37, Pro38 [Trp(02)25, Asp28] Exendin-4(1-39)-NH2,
H-Asn-(Glu)5-des Pro36, Pro37, Pro38 [Trp(02)25, Asp28] Exendin-4(1-39)-NH2,
des Pro36, Pro37, Pro38 [Trp(02)25, Asp28] Exendin-4(1-39)-(Lys)6-NH2,
H-(Lys)6-des Pro36, Pro37, Pro38 [Trp(02)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp (02)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp (02)25, Asp28] Exendin-4(1-39)-(Lys)6-NH2;

or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

BRIEF DESCRIPTION OF THE FIGURES

In the following, the invention will be described by a way of an example and with reference to the schematic drawings in which.

DETAILED DESCRIPTION

Figure 1:
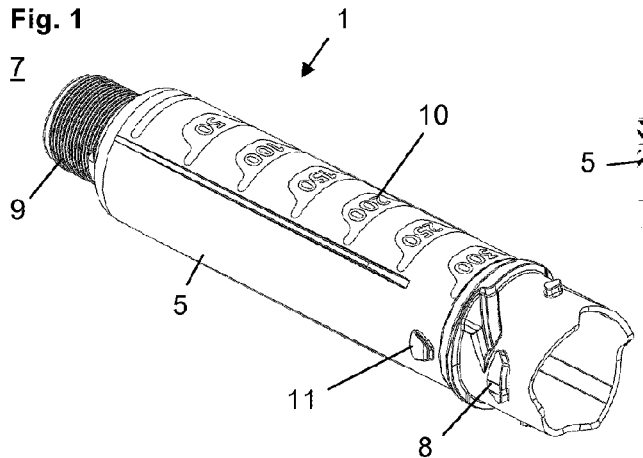
FIG. 1 shows a perspective view of a housing of a cartridge holder according to a first embodiment.
Figure 2:
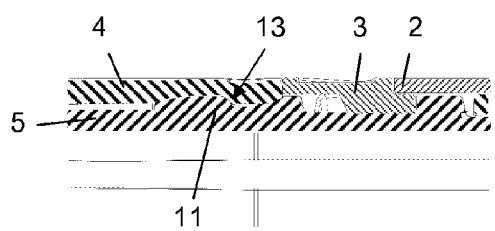
FIG. 2 shows a sectional view of the cartridge holder of FIG. 1 together with a housing and a cap.
Figure 3:
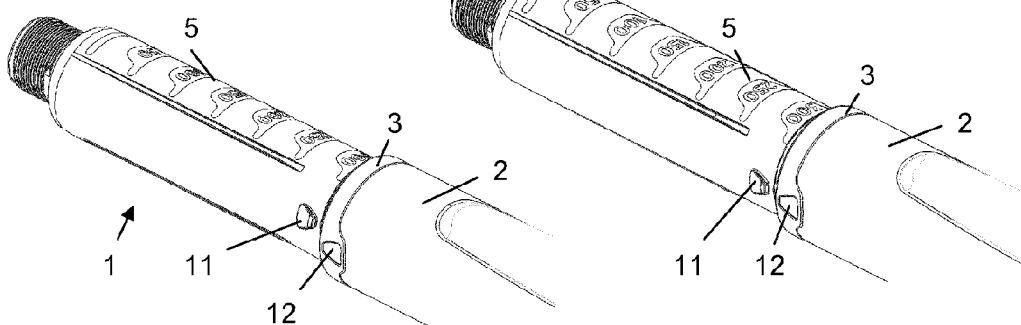
FIG. 3 shows a perspective view of the cartridge holder of FIG. 1 together with a housing in a not fully aligned position.
Figure 4:
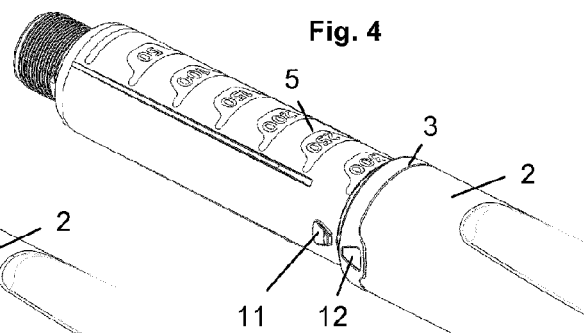
FIG. 4 shows a perspective view of the cartridge holder of FIG. 1 together with a housing in a fully aligned position.

FIG. 1 shows a cartridge holder 1 which can be attached to a drug delivery device (not shown). In FIGS. 2, 3 and 4 an outer housing 2 of the drug delivery device is partly depicted together with an insert or inner housing 3 which is also part of the drug delivery device. Further, FIG. 2 partly shows a cap 4 attached to the cartridge holder 1.

The cartridge holder 1 as depicted in FIG. 1 comprises a sleeve-like body 5 defining a longitudinal axis and having a proximal end 6 and a distal end 7. The proximal end 6 is provided with a series of bayonet lugs 8 serving as engagement means for releasably coupling the cartridge holder 1 to the inner housing 3 of the drug delivery device. The distal end 7 of the cartridge holder 1 is provided with a threaded section 9 for attaching a needle assembly (not shown). A cartridge content scale 10 may be printed on the outer surface of the body 5 which may be made from a transparent or translucent material.

Further, a lug 11 is provided on the outer surface of the body 5 near its proximal end 6. In the embodiment depicted in the Figures, the lug 11 has the shape of a blunted triangular (trapezoidal shape) with one (blunted) tip facing towards the proximal end 6 and one side facing in the distal direction. Further, as can be taken from FIG. 2, lug 11 has an inclined outer surface which is arranged such that the distal side of lug 11 protrudes less from the outer surface of the body compared with the proximal tip of lug 11. In other words, lug 11 has a chamfered outer surface with its height increasing from its distal end to its proximal end.

Although only one lug 11 is depicted in FIGS. 1, 3 and 4, there may be additional lugs 11 on the cartridge holder. Preferably, two lugs 11 are located on opposite sides of the body 5.

When a user attaches the cartridge holder 1 to the drug delivery device, the proximal end 6 of a cartridge holder is introduced into the inner housing 3 and the outer housing 2. The inner housing 3 is provided with a corresponding bayonet structure receiving bayonet lugs 8 to retain the cartridge holder on the drug delivery device. Attachment of cartridge holder 1 in the inner housing 3 includes a relative rotational movement component. In other words, cartridge holder 1 has to be twisted relative to inner housing 3, i.e. relative to the drug delivery device. This can be seen from a comparison of FIGS. 3 and 4 wherein FIG. 3 shows a state where the cartridge holder is not yet fully attached, while FIG. 4 shows a state with the cartridge holder fully attached to the drug delivery device.

To assist a user in recognizing the correct attachment of a cartridge holder, lug 11 serves as an alignment element. A corresponding alignment element 12 is provided on the outer surface of the drug delivery device (in this embodiment the outer surface of the inner housing 3). The corresponding alignment element 12 may have a similar form and/or color as lug 11. In the embodiment of FIGS. 3 and 4, alignment element 12 has a triangular shape with one tip facing in the distal direction. Thus, it is easy for a user to control whether the tips of lug 11 and alignment element 12 face to each other to indicate that the cartridge holder is fully attached. In the embodiment shown in FIGS. 1 to 4, lug 11 has a further function of retaining a cap 4 on the cartridge holder 1. For this purpose, cap 4 is provided with an annular notch 13 on its inner surface. Notch 13 is located such that lug 11 snaps into place in notch 13 if the cap 4 is fully attached to the cartridge holder 1 and thus to the drug delivery device.

Figure 5:
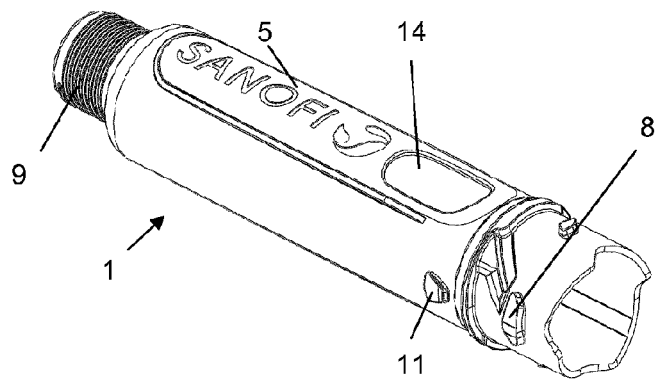
FIG. 5 shows a perspective view of a housing of a cartridge holder according to a second embodiment.

A further embodiment is depicted in FIG. 5 showing the cartridge holder of FIG. 1 from a different point of view. The upper side of cartridge holder 1 of FIG. 1 with the scale 10 is the lower side of the cartridge holder in FIG. 5.

A main aspect of the embodiment of FIG. 5 is an aperture 14 provided in body 5 of the cartridge holder. Aperture 14 may be a hole allowing users to retain control over a cartridge (not shown) which may be received within the cartridge holder. Thus, the risk that the cartridge is inadvertently dropped when fitting or removing the cartridge holder is reduced.

In addition to this function, aperture 14 serves as an alignment element assisting users to recognize the correct attachment of the cartridge holder. In this respect it is preferred if the drug delivery device, for example its inner housing 3 or its outer housing 2, is provided with corresponding alignment elements which are arranged such that aperture 14 and the further alignment element face to each other (align) as soon as the cartridge holder is fully attached to the drug delivery device.

FIG. 5 shows the second embodiment which uses an aperture 14 as alignment feature such that the general design of the cartridge holder 1 is identical or at least similar to that described above with respect to FIG. 1. However, the cartridge holder of the second embodiment may have a different form, in particular it is not necessary for this second embodiment that the lug(s) 11 for retaining the cap are triangular. Differing from FIG. 5, instead of lug(s) 11, the cap may be retained by a bead or an annular rib on the cartridge holder or by respective features provided on the housing of the drug delivery device. Similarly, the embodiment of FIG. 1 does not necessarily require an aperture 14 or the like to use the lug(s) 11 as an alignment feature.

The invention claimed is:
1. A pen-type injector, having
a housing;
a cap; and
a detachable cartridge holder,
wherein the cartridge holder has a longitudinal axis and comprises a body configured to receive a cartridge,
wherein the body comprises:
at a proximal end of the body, a first engagement means for releasably coupling the cartridge holder to the housing,
a latch member for releasably engaging the cap and
a first alignment element which is visual from an outer radial side surface of the body, and
wherein the housing is provided with a second engagement means for releasably coupling the cartridge holder to the housing,
wherein the housing is provided with a second alignment element which is arranged such that the second alignment element faces the first alignment element of the body if the cartridge holder is fully attached to the housing via the first and second engagement means,
wherein the first alignment element is a lug which forms the latch member, wherein the latch member releasably engaging the cap is the first alignment element, wherein the first alignment element is located on the outer radial side surface at the proximal end of the body and the second alignment element is located on an outer radial surface at a distal end of the housing.

2. The pen-type injector according to claim 1, wherein the lug has a trapezoidal or triangular shape in a cross section parallel to the longitudinal axis, wherein the lug is arranged such that a tip or blunted tip is facing towards the proximal end of the body and a side is facing towards a distal end of the body.

3. The pen-type injector according to claim 1, wherein the lug has a chamfered outer surface such that a height of the lug increases in a direction of the longitudinal axis from a distal end of the body to the proximal end of the body.

4. The pen-type injector according to claim 1, wherein a contents scale is provided on the outer side of the body.

5. The pen-type injector according to claim 1, wherein the cap is provided with an annular notch on an inner surface of the cap for receiving the latch member of the body.

6. The pen-type injector according to claim 1, wherein the first engagement means comprise a helical thread.

7. The pen-type injector according to claim 1, wherein the pen-type injector is a resettable injection device.

8. The pen-type injector according to claim 1, wherein the first alignment element has a shape that is the same as a shape of the second alignment element.

9. The pen-type injector according to claim 8, wherein the first alignment element and the second alignment element have a triangular shape.

10. The pen-type injector according to claim 9, wherein a tip of the triangular shape of the first alignment element aligns with a tip of the triangular shape of the second alignment element when the cartridge holder is fully attached to the housing.

11. The pen-type injector according to claim 1, wherein the first alignment element is adjacent to the second alignment element when the cartridge holder is fully attached to the housing.

12. The pen-type injector according to claim 1, wherein the first engagement means comprise a bayonet.

13. A pen-type injector, having
a housing;
a cap; and
a detachable cartridge holder,
wherein the cartridge holder has a longitudinal axis and comprises a body configured to receive a cartridge,
wherein the body comprises:

at a proximal end of the body having an outer radial side surface, a first engagement means for releasably coupling the cartridge holder to the housing, a latch member for releasably engaging the cap and a first alignment element which is visual from an outer side of the body, and wherein the housing is provided with a second engagement means for releasably coupling the cartridge holder to the housing, wherein the housing is provided with a second alignment element which is arranged on an outer radial surface such that the second alignment element faces the first alignment element of the body if the cartridge holder is fully attached to the housing via the first and second engagement means, wherein the first alignment element is a lug which forms the latch member and is located on the outer radial side surface, wherein the latch member releasably engaging the cap is the first alignment element, wherein the first alignment element has a shape that is the same as a shape of the second alignment element.

14. The pen-type injector according to claim 13, wherein the first alignment element and the second alignment element have a triangular shape.

15. The pen-type injector according to claim 14, wherein a tip of the triangular shape of the first alignment element aligns with a tip of the triangular shape of the second alignment element when the cartridge holder is fully attached to the housing.

16. The pen-type injector according to claim 13, wherein the lug has a chamfered outer surface such that a height of the lug increases in a direction of the longitudinal axis from a distal end of the body to the proximal end of the body.

* * * * *